(12) United States Patent
Curry et al.

(10) Patent No.: US 8,321,138 B2
(45) Date of Patent: Nov. 27, 2012

(54) METHOD OF CHARACTERIZING QUALITY OF HYBRIDIZED CGH ARRAYS

(75) Inventors: Bo U. Curry, Redwood City, CA (US); Jayati Ghosh, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1230 days.

(21) Appl. No.: 11/193,912

(22) Filed: Jul. 29, 2005

(65) Prior Publication Data

US 2007/0082338 A1   Apr. 12, 2007

(51) Int. Cl.
G01N 33/48 (2006.01)
C12Q 1/68 (2006.01)
G06F 19/00 (2011.01)

(52) U.S. Cl. .................. 702/19; 435/6; 702/20

(58) Field of Classification Search .......... None
See application file for complete search history.

(56) References Cited

U.S. PATENT DOCUMENTS

| | | | |
|---|---|---|---|
| 5,348,855 A | 9/1994 | Dattagupta et al. | |
| 5,365,455 A * | 11/1994 | Tibbetts et al. ............. | 702/20 |
| 5,447,841 A | 9/1995 | Gray et al. | |
| 5,635,351 A | 6/1997 | Feuerstein et al. | |
| 5,663,319 A | 9/1997 | Bittner et al. | |
| 5,665,549 A | 9/1997 | Pinkel et al. | |
| 5,721,098 A | 2/1998 | Pinkel et al. | |
| 5,776,688 A | 7/1998 | Bittner et al. | |
| 5,830,645 A | 11/1998 | Pinkel et al. | |
| 5,856,097 A | 1/1999 | Pinkel et al. | |
| 5,860,917 A | 1/1999 | Comanor et al. | |
| 5,948,902 A | 9/1999 | Honkanen et al. | |
| 5,965,362 A | 10/1999 | Pinkel et al. | |
| 5,976,790 A | 11/1999 | Pinkel et al. | |
| 6,159,685 A | 12/2000 | Pinkel et al. | |
| 6,171,797 B1 | 1/2001 | Perbost | |
| 6,180,351 B1 | 1/2001 | Cattell | |
| 6,188,969 B1 | 2/2001 | Minor | |
| 6,197,501 B1 | 3/2001 | Cremer et al. | |
| 6,210,878 B1 | 4/2001 | Pinkel et al. | |
| 6,221,583 B1 | 4/2001 | Kayyem et al. | |
| 6,222,664 B1 | 4/2001 | Dorsel | |
| 6,232,072 B1 | 5/2001 | Fisher | |
| 6,242,266 B1 | 6/2001 | Schleifer et al. | |
| 6,251,601 B1 | 6/2001 | Bao et al. | |
| 6,251,685 B1 | 6/2001 | Dorsel et al. | |
| 6,309,822 B1 | 10/2001 | Fodor et al. | |
| 6,320,196 B1 | 11/2001 | Dorsel et al. | |
| 6,323,043 B1 | 11/2001 | Caren et al. | |
| 6,335,167 B1 | 1/2002 | Pinkel et al. | |
| 6,355,921 B1 | 3/2002 | Staton et al. | |
| 6,365,353 B1 | 4/2002 | Lorch et al. | |
| 6,371,370 B2 | 4/2002 | Sadler et al. | |
| 6,406,849 B1 | 6/2002 | Dorsel et al. | |
| 6,410,243 B1 | 6/2002 | Wyrick et al. | |
| 6,432,650 B1 | 8/2002 | Christian et al. | |
| 6,465,182 B1 | 10/2002 | Gray et al. | |
| 6,468,744 B1 | 10/2002 | Cronin et al. | |
| 6,486,457 B1 | 11/2002 | Dorsel et al. | |
| 6,518,556 B2 | 2/2003 | Staton et al. | |
| 6,562,565 B1 | 5/2003 | Pinkel et al. | |
| 6,699,710 B1 | 3/2004 | Kononen et al. | |
| 2002/0006622 A1 | 1/2002 | Bradley et al. | |
| 2002/0028460 A1 | 3/2002 | Pinkel et al. | |
| 2002/0132246 A1 | 9/2002 | Kallioniemi et al. | |
| 2003/0003496 A1 | 1/2003 | Bradley et al. | |
| 2003/0008318 A1 | 1/2003 | Pinkel et al. | |
| 2003/0054388 A1 | 3/2003 | Garner et al. | |
| 2003/0082606 A1 | 5/2003 | Lebo et al. | |
| 2003/0082618 A1 | 5/2003 | Li et al. | |
| 2004/0009493 A1 | 1/2004 | Mohammed et al. | |
| 2004/0063104 A1 | 4/2004 | Amorese et al. | |
| 2004/0132048 A1 | 7/2004 | Martienssen et al. | |
| 2004/0137473 A1 | 7/2004 | Wigler et al. | |
| 2004/0157243 A1 | 8/2004 | Huang et al. | |
| 2004/0248144 A1 | 12/2004 | Mir et al. | |
| 2005/0064406 A1 | 3/2005 | Zabarovsky et al. | |

FOREIGN PATENT DOCUMENTS

| | | | |
|---|---|---|---|
| WO | WO 93/18186 | 9/1993 | |
| WO | WO 98/26098 | 6/1998 | |
| WO | WO 99/00520 | 1/1999 | |
| WO | WO 99/23256 | 5/1999 | |
| WO | WO 01/75160 | 10/2001 | |
| WO | WO 01/90416 | 11/2001 | |
| WO | WO 02/86163 | 4/2002 | |
| WO | WO 03/020898 | 3/2003 | |
| WO | WO 03/027638 | 4/2003 | |
| WO | WO 03/030630 | 4/2003 | |
| WO | WO 03/057923 | 7/2003 | |
| WO | WO 2004/035819 | 4/2004 | |
| WO | WO/2004/058945 | * | 4/2004 |
| WO | WO 2004/088310 | 10/2004 | |
| WO | WO 2004/111267 | 12/2004 | |
| WO | WO2007018656 | 2/2007 | |

OTHER PUBLICATIONS

Karhu et al., Cytometry, 1997, vol. 28, p. 198-205.*
Vermeesch et al., Journal of Histochemistry & Cytochemistry, Mar. 2005, vol. 53, No. 3, p. 413-422.*
Wang et al., Bioinformatics, 2003, vol. 19, No. 11, p. 1341-1347.*
Eilers et al., Bioinformatics, 2005, vol. 21, No. 7, p. 1146-1153, Online publication Nov. 30, 2004.*

(Continued)

Primary Examiner — Pablo Whaley

(57) ABSTRACT

Methods, systems, and computer readable media for determining the quality of a CGH array, including calculating a spread of the derivative of log ratio value differences between consecutive probes representing consecutive positions along a chromosome, wherein ratio values are calculated from probe signals from a CGH array.

8 Claims, 11 Drawing Sheets

OTHER PUBLICATIONS

Davies et al., The Annals of Statistics, 2001, vol. 29, p. 1-65.*
Inazawa et al., Cancer Sci, Jul. 2004, vol. 95, No. 7, p. 559-563.*
Quackenbush (Nature Genetics, 2002, vol. 32, p. 496-501).*
Kallioniemi, et al., "Comparative Genomic Hybridization for Molecular Cytogenetic Analysis of Solid Tumors". Science, vol. 258, Oct. 30, 1992, pp. 818-821.
Rinkel, et al., High Resolution Analysis of DNA Copy Number Variation Using Comparative Genomic Hybridization to Microarrays. vol. 20, Oct. 1998, pp. 207-211.
Pollack, et al., "Genome-Wide Analyis of DNA Copy-Number Changes Using cDNA Microarrays". vol. 23, Sep. 1999, pp. 41-46.
Pollack, et al., "Microarray Analysis Reveals a Major Direct Role of DNA Copy Number Alteration in the Transcriptional Program of Human Breast Tumors". vol. 99, Oct. 1, 2002, pp. 12963-12968.
Schena, et al., Quantitative Monitoring of Gene Expression Patterns with a Complementary DNA Microarray, Science, vol. 270, Oct. 1995, pp. 467-470.
Baldocchi, et al., Oligonucleotide-array-based comparative genomic hybridization. Nature America Inc. http://genetics.nature.com. 1999, 2 pgs.
International Search Report for International Application No. PCT/US06/1782, dated Sep. 14, 2007, 1 page.

* cited by examiner

QC Metrics table

QC Metrics

| Array Name | Design No. | QC Status | DLRSpr... | SignalT... | SignalT... | SignalE... | SignalE... | IntraAr... | IntraAr... |
|---|---|---|---|---|---|---|---|---|---|
| K562vXY-0.1 | 012700 | Pass | 0.0500400l... | 29.0704778... | 14.7285517... | 63.22.82 | 64.5045 | 0.19089997... | 0.15823321 |
| K562vXY-0.1b | 012700 | Pass | 0.05394849... | 0.05394849... | 82.9381058... | 272.489 | 99.444 | 0.44962032... | 0.28041878 |
| K562vXY-5 | 012700 | Pass | 0.05960898... | 29.0704778... | 14.7285517... | 63.22.82 | 64.5045 | 0.19089997... | 0.15823321 |
| K562vXY-5b | 012700 | Pass | 0.02820375... | 14.1336666... | 92.5872338... | 410.567 | 293.792 | 0.17785640... | 0.13218889 |
| K562vXY+0.1 | 012700 | Pass | 0.03956669... | 76.1738823... | 49.0944906... | 131.342 | 106.319 | 0.25517261... | 0.43801493 |
| K562vXY+0.1 | 012700 | Pass | 0.03568135... | 36.6533823... | 50.1235748... | 112.152 | 80.5451 | 0.40516065... | 0.35478620 |
| K562vXY+0.1b | 012700 | Pass | 0.06296005... | 32.7224899... | 36.5342369... | 199.569 | 206.977 | 0.34351521... | 0.49271257 |
| K562vXY+5 | 012700 | Fail | 0.04035373... | 46.71113537... | 46.6160252... | 133.106 | 69.3105 | 0.32124803... | 0.42022920 |
| K562vXY+5b | 012700 | Marginal | 0.03019760... | 23.1236946... | 97.3305087... | 465.416 | 337.729 | 0.20090433... | 0.28580572 |
|  | 012700 | NA | 0.05888010... | 82.1095753... | 24.1269317... | 79.7605 | 81.994 | 0.07891259... | 0.25437057 |

Group By [Comments ▷]   [Show Frequency Distribution]   [Plot]   [Select All]   [Deselect All]   [Close]

FIG. 11

METHOD OF CHARACTERIZING QUALITY OF HYBRIDIZED CGH ARRAYS

BACKGROUND OF THE INVENTION

Many genomic and genetic studies are directed to the identification of differences in gene dosage or expression among cell populations for the study and detection of disease. For example, many malignancies involve the gain or loss of DNA sequences (alterations in copy number), sometimes entire chromosomes, that may result in activation of oncogenes or inactivation of tumor suppressor genes. Identification of the genetic events leading to neoplastic transformation and subsequent progression can facilitate efforts to define the biological basis for disease, improve prognostication of therapeutic response, and permit earlier tumor detection. In addition, perinatal genetic problems frequently result from loss or gain of chromosome segments such as trisomy 21 or the micro deletion syndromes. Trisomy of chromosome 13 results in Patau syndrome. Abnormal numbers of sex chromosomes result in various developmental disorders. Thus, methods of prenatal detection of such abnormalities can be helpful in early diagnosis of disease.

Comparative genomic hybridization (CGH) is a technique that is used to evaluate variations in genomic copy number in cells. In one implementation of CGH, genomic DNA is isolated from normal reference cells, as well as from test cells (e.g., tumor cells). The two nucleic acids are differentially labeled and then simultaneously hybridized in situ to metaphase chromosomes of a reference cell. Chromosomal regions in the test cells which are at increased or decreased copy number can be identified by detecting regions where the ratio of signal from the two distinguishably labeled nucleic acids is altered. For example, those regions that have been decreased in copy number in the test cells will show relatively lower signal from the test DNA that the reference shows, compared to other regions of the genome. Regions that have been increased in copy number in the test cells will show relatively higher signal from the test DNA.

A recent technology development introduced an oligonucleotide array platform for array based comparative genomic hybridization (aCGH) analyses. Such approaches offer benefits over immobilized chromosome approaches, including a higher resolution, as defined by the ability of the assay to localize chromosomal alterations to specific areas of the genome. For further detailed description regarding aCGH technology, the reader is referred to co-pending application Ser. No. 10/744,495 filed Dec. 22, 2003 and titled "Comparative Genomic Hybridization Assays Using Immobilized Oligonucleotide Features and Compositions for Practicing the Same", which is incorporated herein, in its entirety, by reference thereto.

When processing aCGH data, it is important to have confidence in the quality of the array or arrays from which the data was generated. Accordingly, there is a need for quality assessment and analysis of CGH arrays to inform the user of the quality of arrays from which CGH data are extracted so that only arrays having at least a minimum level of measured qualities (which may be set by the user and/or according to the type of research being conducted) are relied upon for data before it is further processed.

SUMMARY OF THE INVENTION

Methods, systems and computer readable media are provided for characterizing quality of CGH arrays, including generating at least one metric for a CGH array that characterizes a property of the CGH array; repeating the generation of at least one metric for at least one additional CGH array; and comparing each metric across all CGH array metric values generated to identify a quality of any one of the CGH arrays characterized, relative to the CGH arrays characterized for that metric.

Methods, systems and computer readable media are provided for determining the quality of a CGH array, including calculating a spread of the derivative of log ratio value differences between consecutive probes representing consecutive positions along a chromosome, wherein ratio values are calculated from probe signals from a CGH array, as read by a reader on first and second channels thereof, or from probes signals from two CGH arrays, as read by a single channel reader.

Methods, systems and computer readable media are provided for qualifying a CGH array, including quantifying an interarray reproducibility metric characterizing selected sets of probe replicates.

Methods, systems and computer readable media are provided for qualifying a CGH array, including generating a Receiver Operating Characteristic (ROC) curve and analyzing false positive and true positive signals from a normal male sample and a normal female sample, as read by a reader on first and second channels thereof, or from one of a normal male sample and a normal female sample on the CGH array and the other of the normal male sample and normal female sample on a second CGH array, as read by a single-channel reader.

Methods, systems and computer readable media are provided for determining the quality of a CGH array are provided, including segmenting, by copy number, log ratio signals from probes on the CGH array representing a genome; plotting a probability distribution of the segmented log ratio values; and quantifying separation between copy number peaks resulting from the plotting of the probability distribution.

These and other advantages and features of the invention will become apparent to those persons skilled in the art upon reading the details of the methods, systems and computer readable media as more fully described below.

BRIEF DESCRIPTION OF THE DRAWINGS

FIG. 11 shows a display of a metrics table reporting metrics for a plurality of arrays.

DETAILED DESCRIPTION OF THE INVENTION

Figure 1:
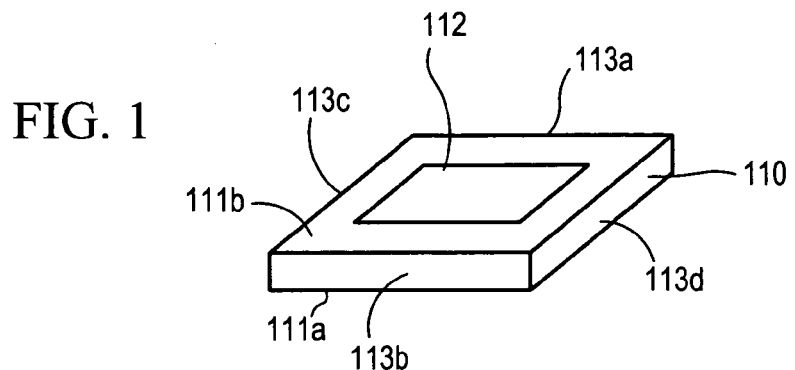
FIG. 1 shows an exemplary substrate carrying an array, such as used for CGH, such as may be used to extract and analyzed signals using systems and methods described herein.

Before the present systems, methods and computer readable media are described, it is to be understood that this invention is not limited to particular systems, methods and computer readable media described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a probe" includes a plurality of such probes and reference to "the chromosome" includes reference to one or more chromosomes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A chemical "array", unless a contrary intention appears, includes any one, two or three-dimensional arrangement of addressable regions bearing a particular chemical moiety or moieties (for example, biopolymers such as polynucleotide sequences) associated with that region, where the chemical moiety or moieties are immobilized on the surface in that region. By "immobilized" is meant that the moiety or moieties are stably associated with the substrate surface in the region, such that they do not separate from the region under conditions of using the array, e.g., hybridization and washing and stripping conditions. As is known in the art, the moiety or moieties may be covalently or non-covalently bound to the surface in the region. For example, each region may extend into a third dimension in the case where the substrate is porous while not having any substantial third dimension measurement (thickness) in the case where the substrate is non-porous. An array may contain more than ten, more than one hundred, more than one thousand more than ten thousand features, or even more than one hundred thousand features, in an area of less than 20 cm$^2$ or even less than 10 cm$^2$. For example, features may have widths (that is, diameter, for a round spot) in the range of from about 10 μm to about 1.0 cm. In other embodiments each feature may have a width in the range of about 1.0 μm to about 1.0 mm, such as from about 5.0 μm to about 500 μm, and including from about 10 μm to about 200 μm. Non-round features may have area ranges equivalent to that of circular features with the foregoing width (diameter) ranges. A given feature is made up of chemical moieties, e.g., nucleic acids, that bind to (e.g., hybridize to) the same target (e.g., target nucleic acid), such that a given feature corresponds to a particular target. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide. Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations. An array is "addressable" in that it has multiple regions (sometimes referenced as "features" or "spots" of the array) of different moieties (for example, different polynucleotide sequences) such that a region at a particular predetermined location (an "address") on the array will detect a particular target or class of targets (although a feature may incidentally detect non-targets of that feature). The target for which each feature is specific is, in representative embodiments, known. An array feature is generally homogeneous in composition and concentration and the features may be separated by intervening spaces (although arrays without such separation can be fabricated).

In the case of an array, the "target" will be referenced as a moiety in a mobile phase (typically fluid), to be detected by probes ("target probes") which are bound to the substrate at the various regions. However, either of the "target" or "target probes" may be the one which is to be detected by the other (thus, either one could be an unknown mixture of polynucleotides to be detected by binding with the other). "Addressable sets of probes" and analogous terms refer to the multiple regions of different moieties supported by or intended to be supported by the array surface.

The term "sample" as used herein relates to a material or mixture of materials, containing one or more components of interest. Samples include, but are not limited to, samples obtained from an organism or from the environment (e.g., a soil sample, water sample, etc.) and may be directly obtained from a source (e.g., such as a biopsy or from a tumor) or indirectly obtained e.g., after culturing and/or one or more processing steps. In one embodiment, samples are a complex mixture of molecules, e.g., comprising at least about 50 different molecules, at least about 100 different molecules, at least about 200 different molecules, at least about 500 different molecules, at least about 1000 different molecules, at least about 5000 different molecules, at least about 10,000 molecules, etc.

The term "genome" refers to all nucleic acid sequences (coding and non-coding) and elements present in any virus, single cell (prokaryote and eukaryote) or each cell type in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3.0 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence. In certain aspects, a "genome" refers to nuclear nucleic acids, excluding mitochondrial nucleic acids; however, in other aspects, the term does not exclude mitochondrial nucleic acids. In still other aspects, the "mitochondrial genome" is used to refer specifically to nucleic acids found in mitochondrial fractions.

By "genomic source" is meant the initial nucleic acids that are used as the original nucleic acid source from which the probe nucleic acids are produced, e.g., as a template in the nucleic acid amplification and/or labeling protocols.

If a surface-bound polynucleotide or probe "corresponds to" a chromosomal region, the polynucleotide usually contains a sequence of nucleic acids that is unique to that chromosomal region. Accordingly, a surface-bound polynucleotide that corresponds to a particular chromosomal region usually specifically hybridizes to a labeled nucleic acid made from that chromosomal region, relative to labeled nucleic acids made from other chromosomal regions.

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

The phrase "oligonucleotide bound to a surface of a solid support" or "probe bound to a solid support" or a "target bound to a solid support" refers to an oligonucleotide or mimetic thereof, e.g., PNA, LNA or UNA molecule that is immobilized on a surface of a solid substrate, where the substrate can have a variety of configurations, e.g., a sheet, bead, particle, slide, wafer, web, fiber, tube, capillary, microfluidic channel or reservoir, or other structure. In certain embodiments, the collections of oligonucleotide elements employed herein are present on a surface of the same planar support, e.g., in the form of an array. It should be understood that the terms "probe" and "target" are relative terms and that a molecule considered as a probe in certain assays may function as a target in other assays.

As used herein, a "test nucleic acid sample" or "test nucleic acids" refer to nucleic acids comprising sequences whose quantity or degree of representation (e.g., copy number) or sequence identity is being assayed. Similarly, "test genomic acids" or a "test genomic sample" refers to genomic nucleic acids comprising sequences whose quantity or degree of representation (e.g., copy number) or sequence identity is being assayed.

As used herein, a "reference nucleic acid sample" or "reference nucleic acids" refers to nucleic acids comprising sequences whose quantity or degree of representation (e.g., copy number) or sequence identity is known. Similarly, "reference genomic acids" or a "reference genomic sample" refers to genomic nucleic acids comprising sequences whose quantity or degree of representation (e.g., copy number) or sequence identity is known. A "reference nucleic acid sample" may be derived independently from a "test nucleic acid sample," i.e., the samples can be obtained from different organisms or different cell populations of the sample organism. However, in certain embodiments, a reference nucleic acid is present in a "test nucleic acid sample" which comprises one or more sequences whose quantity or identity or degree of representation in the sample is unknown while containing one or more sequences (the reference sequences) whose quantity or identity or degree of representation in the sample is known. The reference nucleic acid may be naturally present in a sample (e.g., present in the cell from which the sample was obtained) or may be added to or spiked in the sample.

If a surface-bound polynucleotide or probe "corresponds to" a chromosome, the polynucleotide usually contains a sequence of nucleic acids that is unique to that chromosome. Accordingly, a surface-bound polynucleotide that corresponds to a particular chromosome usually specifically hybridizes to a labeled nucleic acid made from that chromosome, relative to labeled nucleic acids made from other chromosomes. Array features, because they usually contain surface-bound polynucleotides, can also correspond to a chromosome.

A "non-cellular chromosome composition" is a composition of chromosomes synthesized by mixing pre-determined amounts of individual chromosomes. These synthetic compositions can include selected concentrations and ratios of chromosomes that do not naturally occur in a cell, including any cell grown in tissue culture. Non-cellular chromosome compositions may contain more than an entire complement of chromosomes from a cell, and, as such, may include extra copies of one or more chromosomes from that cell. Non-cellular chromosome compositions may also contain less than the entire complement of chromosomes from a cell.

"CGH" or "Comparative Genomic Hybridization" refers generally to techniques for identification of chromosomal alterations (such as in cancer cells, for example). Using CGH, ratios between tumor or test sample and normal or control sample enable the detection of chromosomal amplifications and deletions of regions that may include oncogenes and tumor suppressive genes, for example.

A "CGH array" or "aCGH array" refers to an array that can be used to compare DNA samples for relative differences in copy number. In general, an aCGH array can be used in any assay in which it is desirable to scan a genome with a sample of nucleic acids. For example, an aCGH array can be used in location analysis as described in U.S. Pat. No. 6,410,243, the entirety of which is incorporated herein. In certain aspects, a CGH array provides probes for screening or scanning a genome of an organism and comprises probes from a plurality of regions of the genome. In one aspect, the array comprises probe sequences for scanning an entire chromosome arm, wherein probes targets are separated by at least about 500 bp, at least about 1 kb, at least about 5 kb, at least about 10 kb, at least about 25 kb, at least about 50 kb, at least about 100 kb, at least about 250 kb, at least about 500 kb and at least about 1 Mb. In another aspect, the array comprises probes sequences for scanning an entire chromosome, a set of chromosomes, or the complete complement of chromosomes forming the organism's genome. By "resolution" is meant the spacing on the genome between sequences found in the probes on the array. In some embodiments (e.g., using a large number of probes of high complexity) all sequences in the genome can be present in the array. The spacing between different locations of the genome that are represented in the probes may also vary, and may be uniform, such that the spacing is substantially the same between sampled regions, or non-uniform, as desired. An assay performed at low resolution on one array, e.g., comprising probe targets separated by larger distances, may be repeated at higher resolution on another array, e.g., comprising probe targets separated by smaller distances.

In certain aspects, in constructing the arrays, both coding and non-coding genomic regions are included as probes, whereby "coding region" refers to a region comprising one or more exons that is transcribed into an mRNA product and from there translated into a protein product, while by non-coding region is meant any sequences outside of the exon regions, where such regions may include regulatory sequences, e.g., promoters, enhancers, untranslated but transcribed regions, introns, origins of replication, telomeres, etc. In certain embodiments, one can have at least some of the probes directed to non-coding regions and others directed to coding regions. In certain embodiments, one can have all of the probes directed to non-coding sequences. In certain embodiments, one can have all of the probes directed to coding sequences. In certain other aspects, individual probes comprise sequences that do not normally occur together, e.g., to detect gene rearrangements, for example.

In some embodiments, at least 5% of the polynucleotide probes on the solid support hybridize to regulatory regions of a nucleotide sample of interest while other embodiments may have at least 30% of the polynucleotide probes on the solid support hybridize to exonic regions of a nucleotide sample of interest. In yet other embodiments, at least 50% of the polynucleotide probes on the solid support hybridize to intergenic (e.g., non-coding) regions of a nucleotide sample of interest. In certain aspects, probes on the array represent random selection of genomic sequences (e.g., both coding and non-coding). However, in other aspects, particular regions of the genome are selected for representation on the array, e.g., such as CpG islands, genes belonging to particular pathways of interest or whose expression and/or copy number are associated with particular physiological responses of interest (e.g., disease, such a cancer, drug resistance, toxological responses and the like). In certain aspects, where particular genes are identified as being of interest, intergenic regions proximal to those genes are included on the array along with, optionally, all or portions of the coding sequence corresponding to the genes. In one aspect, at least about 100 bp, 500 bp, 1,000 bp, 5,000 bp, 10,000 kb or even 100,000 kb of genomic DNA upstream of a transcriptional start site is represented on the array in discrete or overlapping sequence probes. In certain aspects, at least one probe sequence comprises a motif sequence to which a protein of interest (e.g., such as a transcription factor) is known or suspected to bind.

In certain aspects, repetitive sequences are excluded as probes on the arrays. However, in another aspect, repetitive sequences are included.

The choice of nucleic acids to use as probes may be influenced by prior knowledge of the association of a particular chromosome or chromosomal region with certain disease conditions. International Application WO 93/18186 provides a list of exemplary chromosomal abnormalities and associated diseases, which are described in the scientific literature. Alternatively, whole genome screening to identify new regions subject to frequent changes in copy number can be performed using the methods of the present invention discussed further below.

In some embodiments, previously identified regions from a particular chromosomal region of interest are used as probes. In certain embodiments, the array can include probes which "tile" a particular region (e.g., which have been identified in a previous assay or from a genetic analysis of linkage), by which is meant that the probes correspond to a region of interest as well as genomic sequences found at defined intervals on either side, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses tiled array tailored to the initially identified region to further assay the region at a higher resolution, e.g., in an iterative protocol.

In certain aspects, the array includes probes to sequences associated with diseases associated with chromosomal imbalances for prenatal testing. For example, in one aspect, the array comprises probes complementary to all or a portion of chromosome 21 (e.g., Down's syndrome), all or a portion of the X chromosome (e.g., to detect an X chromosome deficiency as in Turner's Syndrome) and/or all or a portion of the Y chromosome Klinefelter Syndrome (to detect duplication of an X chromosome and the presence of a Y chromosome), all or a portion of chromosome 7 (e.g., to detect William's Syndrome), all or a portion of chromosome 8 (e.g., to detect Langer-Giedon Syndrome), all or a portion of chromosome 15 (e.g., to detect Prader-Willi or Angelman's Syndrome, all or a portion of chromosome 22 (e.g., to detect Di George's syndrome).

Other "themed" arrays may be fabricated, for example, arrays including whose duplications or deletions are associated with specific types of cancer (e.g., breast cancer, prostate cancer and the like). The selection of such arrays may be based on patient information such as familial inheritance of particular genetic abnormalities. In certain aspects, an array for scanning an entire genome is first contacted with a sample and then a higher-resolution array is selected based on the results of such scanning.

Themed arrays also can be fabricated for use in gene expression assays, for example, to detect expression of genes involved in selected pathways of interest, or genes associated with particular diseases of interest.

In one embodiment, a plurality of probes on the array are selected to have a duplex $T_m$ within a predetermined range. For example, in one aspect, at least about 50% of the probes have a duplex $T_m$ within a temperature range of about 75° C. to about 85° C. In one embodiment, at least 80% of said polynucleotide probes have a duplex $T_m$ within a temperature range of about 75° C. to about 85° C., within a range of about 77° C. to about 83° C., within a range of from about 78° C. to about 82° C. or within a range from about 79° C. to about 82° C. In one aspect, at least about 50% of probes on an array have range of $T_m$'s of less than about 4° C., less then about 3° C., or even less than about 2° C., e.g., less than about 1.5° C., less than about 1.0° C. or about 0.5° C.

The probes on the microarray, in certain embodiments have a nucleotide length in the range of at least 30 nucleotides to 200 nucleotides, or in the range of at least about 30 to about 150 nucleotides. In other embodiments, at least about 50% of the polynucleotide probes on the solid support have the same nucleotide length, and that length may be about 60 nucleotides.

In certain aspects, longer polynucleotides may be used as probes. In addition to the oligonucleotide probes described above, cDNAs, or inserts from phage BACs (bacterial artificial chromosomes) or plasmid clones, can be arrayed. Probes may therefore also range from about 201-5000 bases in length, from about 5001-50,000 bases in length, or from about 50,001-200,000 bases in length, depending on the platform used. If other polynucleotide features are present on a subject array, they may be interspersed with, or in a separately-hybridizable part of the array from the subject oligonucleotides.

In still other aspects, probes on the array comprise at least coding sequences.

In one aspect, probes represent sequences from an organism such as *Drosophila melanogaster, Caenorhabditis elegans*, yeast, zebrafish, a mouse, a rat, a domestic animal, a companion animal, a primate, a human, etc. In certain aspects, probes representing sequences from different organisms are provided on a single substrate, e.g., on a plurality of different arrays.

A "CGH assay" using an aCGH array can be generally performed as follows. In one embodiment, a population of nucleic acids contacted with an aCGH array comprises at least two sets of nucleic acid populations, which can be derived from different sample sources. For example, in one aspect, a target population contacted with the array comprises a set of target molecules from a reference sample and from a test sample. In one aspect, the reference sample is from an organism having a known genotype and/or phenotype, while the test sample has an unknown genotype and/or phenotype or a genotype and/or phenotype that is known and is different from that of the reference sample. For example, in one aspect, the reference sample is from a healthy patient while the test sample is from a patient suspected of having cancer or known to have cancer.

In one embodiment, a target population being contacted to an array in a given assay comprises at least two sets of target populations that are differentially labeled (e.g., by spectrally distinguishable labels). In one aspect, control target molecules in a target population are also provided as two sets, e.g., a first set labeled with a first label and a second set labeled with a second label corresponding to first and second labels being used to label reference and test target molecules, respectively.

In one aspect, the control target molecules in a population are present at a level comparable to a haploid amount of a gene represented in the target population. In another aspect, the control target molecules are present at a level comparable to a diploid amount of a gene. In still another aspect, the control target molecules are present at a level that is different from a haploid or diploid amount of a gene represented in the target population. The relative proportions of complexes formed labeled with the first label vs. the second label can be used to evaluate relative copy numbers of targets found in the two samples.

In certain aspects, test and reference populations of nucleic acids may be applied separately to separate but identical arrays (e.g., having identical probe molecules) and the signals from each array can be compared to determine relative copy numbers of the nucleic acids in the test and reference populations.

Methods to fabricate arrays are described in detail in U.S. Pat. Nos. 6,242,266; 6,232,072; 6,180,351; 6,171,797 and 6,323,043. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample and then read. Reading of an array may be accomplished by illuminating the array and reading the location and intensity of resulting fluorescence at multiple regions on each feature of the array. For example, a scanner may be used for this purpose is the AGILENT MICROARRAY SCANNER manufactured by Agilent Technologies, Palo, Alto, Calif. or other similar scanner. Other suitable apparatus and methods are described in U.S. Pat. Nos. 6,518, 556; 6,486,457; 6,406,849; 6,371,370; 6,355,921; 6,320,196; 6,251,685 and 6,222,664. Scanning typically produces a scanned image of the array which may be directly inputted to a feature extraction system for direct processing and/or saved in a computer storage device for subsequent processing. However, arrays may be read by any other methods or apparatus than the foregoing, other reading methods including other optical techniques or electrical techniques (where each feature is provided with an electrode to detect bonding at that feature in a manner disclosed in U.S. Pat. Nos. 6,251,685, 6,221,583 and elsewhere).

An array is "addressable" when it has multiple regions of different moieties, i.e., features (e.g., each made up of different oligonucleotide sequences) such that a region (i.e., a "feature" or "spot" of the array) at a particular predetermined location (i.e., an "address") on the array will detect a particular solution phase nucleic acid sequence. Array features are typically, but need not be, separated by intervening spaces.

Figure 2:
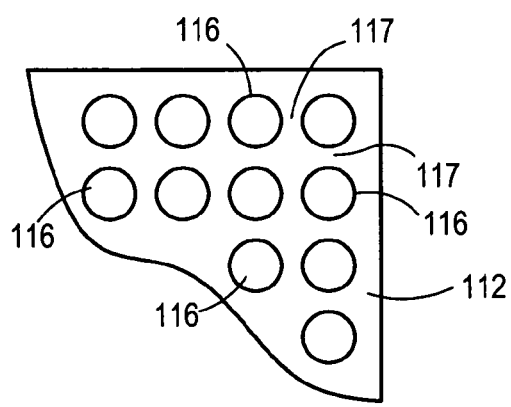
FIG. 2 shows an enlarged view of a portion of FIG. 1 showing spots or features.
Figure 3:
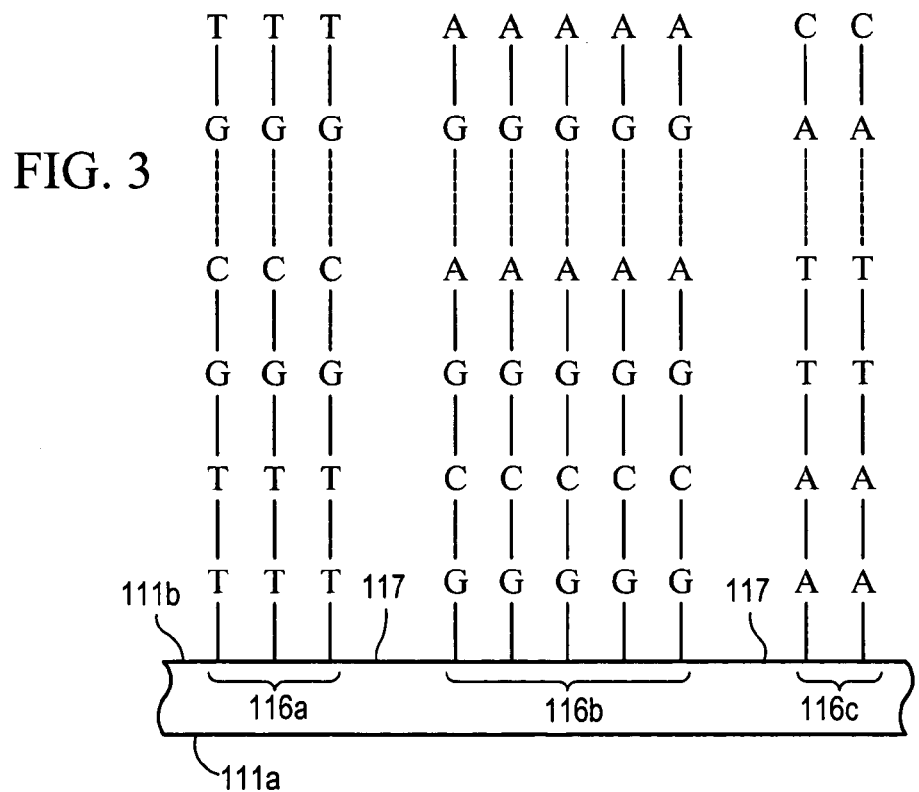
FIG. 3 is an enlarged view of a portion of the substrate of FIG. 1.

An exemplary array is shown in FIGS. 1-3, where the array shown in this representative embodiment includes a contiguous planar substrate 110 carrying an array 112 disposed on a rear surface 111b of substrate 110. It will be appreciated though, that more than one array (any of which are the same or different) may be present on rear surface 111b, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the rear surface 111b, with regions of the rear surface 111b adjacent the opposed sides 113c, 113d and leading end 113a and trailing end 113b of slide 110, not being covered by any array 112. A front surface 111a of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of oligomers, e.g., in the form of polynucleotides, and specifically oligonucleotides. As mentioned above, all of the features 116 may be different, or some or all could be the same. The interfeature areas 117 could be of various sizes and configurations. Each feature carries a predetermined oligomer such as a predetermined polynucleotide (which includes the possibility of mixtures of polynucleotides). It will be understood that there may be a linker molecule (not shown) of any known types between the rear surface 111b and the first nucleotide.

Substrate 110 may carry on front surface 111a, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

In the case of an array in the context of the present application, the "target" may be referenced as a moiety in a mobile phase (typically fluid), to be detected by "probes" which are bound to the substrate at the various regions.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

A "design file" is typically provided by an array manufacturer and is a file that embodies all the information that the array designer from the array manufacturer considered to be pertinent to array interpretation. For example, Agilent Technologies supplies its array users with a design file written in the XML language that describes the geometry as well as the biological content of a particular array.

A "design pattern" is a description of relative placement of features, with annotation. A grid template or design pattern can be generated from parsing a design file and can be saved/stored on a computer storage device. A grid template has basic grid information from the design file that it was generated from, which information may include, for example, the number of rows in the array from which the grid template was generated, the number of columns in the array from which the grid template was generated, column spacings, subgrid row and column numbers, if applicable, spacings between subgrids, number of arrays/hybridizations on a slide, etc. An alternative way of creating a grid template is by using an interactive grid mode provided by the system, which also provides the ability to add further information, for example, such as subgrid relative spacings, rotation and skew information, etc.

A "property" of an array, as used herein refers to a characteristic of an array that may be measured through analysis and calculation based on signals received during reading (e.g., scanning or other method of obtaining signals from) the array, and which may be used as a measure of quality of the array. Properties include, but are not limited to, noise, signal-to-noise, background signal, signal intensity, uniformity/non-uniformity, etc.

A "probe signal", "probe value" or "probe signal value" refers to the ratio of a signal obtained from the probe to the signal of a target hybridized thereto, i.e., the signal from a probe bound to a target.

When one item is indicated as being "remote" from another, this is referenced that the two items are not at the same physical location, e.g., the items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer. Where the processor is programmable, suitable programming can be communicated from a remote location to the processor, or previously saved in a computer program product. For example, a magnetic or optical disk may carry the programming, and can be read by a suitable disk reader communicating with each processor at its corresponding station.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

The present invention provides a variety of metrics that provide objective measurements adapted to gauge the quality of CGH arrays. Quality, as used herein is a relative indicator of the reliability of the information (signals) that are read from the probes on an array and relates to the degree of confidence with which a user can rely upon the results produced by such array. Such metrics may be calculated and outputted to a statistics file or table and or posted to a QC Report. Plots may be generated from calculated metrics and posted to the QC Report.) In addition to a statistics table in the textual output, feature extraction measurements may also be outputted. The calculation of metrics is objective and produces values that can be tracked over time (e.g. using a compilation of statistics table outputs).

The metrics calculated may make use of knowledge of specific processes, when known, including, but not limited to those used in probe selection, synthesis, target preparation (including, but not limited to processes such as labeling, amplification and the like), hyb, wash and/or stripping procedures, scanning, and feature extraction of chemical arrays. All of these metrics provided are also applicable for quality control of those CGH arrays for which specific processes are not known.

Metrics may exclude a consideration of features based upon one or more filters that can be applied. One such filter determines if a feature or background region is non-uniform and/or a population outlier, and the system is configured to automatically flag such non- uniform features and population outliers. This function may currently be performed by feature extraction software designed to extract signals from the array. Further details about filtering for feature non-uniformity and/or outliers, as well as other types of filtering can be found in co-pending, application Ser. No. 11/192,680 filed Jul. 29, 2005 concurrently herewith and titled "System and Methods for Characterization of Chemical Arrays for Quality Control", which is hereby incorporated herein, in its entirety, by reference thereto. Further, metrics may be adapted to filter features to consider specific sequence types of features as a basis for a metric calculation. For example, metrics include filters to consider only one, or a specified number of the probes types including positive controls, negative controls, spike-in controls and experimental probes (i.e., "non-control probes"). In addition, in one aspect, the software of the system is designed to be modifiable to allow changes to control types that may be filtered and/or identification of sub- types of probes for filtering purposes. Further, filtering may be implemented to consider a specified feature signal range and/or a specified log-ratio significance level. Still further, for those metrics that calculate summary statistics (e.g., averages, standard deviations, etc.) based upon a population of features or background regions, the user can set, in the protocol, the minimum number of features or background regions that need to be present in order to allow the calculation of such summary statistics. Indeed, all the above filters may be user-customizable.

Metrics for selected arrays may be displayed in a QC report in the form of one or more run charts or histograms. For a run chart, the data points along the X-axis denote individual arrays and the Y-axis denotes the corresponding metric value being reported. Thus, for each metric, a plot may be provided across selected individual arrays. When a histogram is plotted, the X-axis denotes the bins on metric values and the Y-axis denotes the number of arrays in the metric value range of the corresponding bin. The total number of bins displayed may be selectable by a user. A histogram may be defined for each metric in this manner. Histogram plots facilitate the selection of threshold values for the metrics being reported on. These features are described in more detail below.

Numeric values of metrics can be compared to thresholds and warnings shown for those that are over or under given thresholds. Thresholds can be obtained in several manners, including, but not limited to the following examples. When chemical arrays are provided for which the entire chain of production processes is known, the software component of the system may include lists of thresholds that are appropriate for different specified groups of processes, and these lists can be updated, as needed. Alternatively, users may supply their own lists of thresholds that can be used to qualify CGH arrays.

One metric outputted by the present system is referred to as the "noise estimate", which calculates an average estimate of noise over the CGH array. Negative control probes are designed not to bind to any genetic material and theoretically should output a zero signal level. Negative control probes (control type=−1) are typically located at random locations across the CGH array, one of the uses of such probes being to analyze the signal thereof to give the estimate of noise from the array. The noise estimate metric may be performed to calculate the standard deviation of the signals read from the negative control probes.

Background subtracted signals from the negative control probes are the signal values that are typically used to calculate the noise estimate. The background levels (i.e., background signal) that are subtracted from the negative control signals may be calculated in different ways. For example, a surface may be fitted over all of the negative controls, and the values on the surface may be taken as background levels, so that the value of background for a feature may be taken as the means signal value of the feature at the centroid of the feature for which a background value is sought, for example. Ideally the distribution of negative control probes after proper background subtraction will be centered around a value of zero with a spread, which is calculated by the present methods. One alternative method of calculating the background level is to calculate the median value of the negative control signals. The background subtracted signals are then calculated as: background subtracted signal=mean signal−background signal, wherein the mean signal is the mean value of pixel signals from the pixels located within the feature for which the background subtracted signal is being calculated, and the background signal. A background subtracted signal for each probe on the CGH array may be calculated in this manner.

The background subtracted signals for the negative control probes are then considered and a standard deviation of these signals is calculated to show the negative control signal spread. Assuming that there is no binding to the negative control probes, the background subtracted signals from the negative control probes should be close to zero, and the standard deviation (spread) of these signals is an indicator of the noise level across the CGH array.

One filter provided by the system determines if a feature or background region is non-uniform and/or a population outlier, and the system is configured to automatically flag such non-uniform features and population outliers. Filtering may be performed for noise estimate procedures, so that any negative control feature that has been determined to be a non-uniform outlier is not considered in the noise estimate calculations. The noise estimate metric may be calculated for a single channel array, as well as for each channel of a multi-channel array.

Another metric that may be calculated by the system is the median signal intensity of the background subtracted signal, or "signal estimate". Filtering may be applied when calculating this metric so that any feature that has been determined to have a saturated signal level (i.e., at that maximum signal value for the dynamic range of the scanner) and/or to be non-uniform, is not considered for these calculations. The remaining background subtracted signals are then sorted to identify the median background subtracted signal level (e.g., the $50^{th}$ percentile value may be taken. An interesting characteristic of CGH arrays is that most of the signal values on such an array will typically be very similar. That is, most of the probes on the array will generate "normal signals", indicating that no amplification or deletion has occurred on that portion of the chromosome represented by that particular probe. Therefore, the median signal intensity of the background subtracted signals is also expected to be at the "normal" value, since only a very small number of probes should have values deviating significantly from the values of the majority of the probes. Thus, the median signal intensity of the background subtracted signals is generally indicative of the array intensity. This normal value is generally predictable and thresholds can be preset, or settable by a user, to identify when the median signal intensity of the background subtracted signals exceeds an upper or lower threshold. In such an occurrence, a user is on notice that the array being reported upon may not be a reliable source of information. Causes for a low or high result exceeding a low or high threshold value respectively, may be numerous, and can include, for example, poor probe selection in designing the CGH array, as well as various preparation and processing errors, including hybridization and wash errors, etc.

A further metric for characterizing CGH array is referred to as "signal-to-noise ratio". This metric may be calculated by dividing the median signal intensity of the background subtracted signals by the standard deviation of the negative control signals, both of which were described in detail above. The signal to noise ratio is a quantitative value describing the relative quality of a CGH array regarding its ability to output signal values that may be clearly differentiated from the noise level of the array.

Figure 4A:
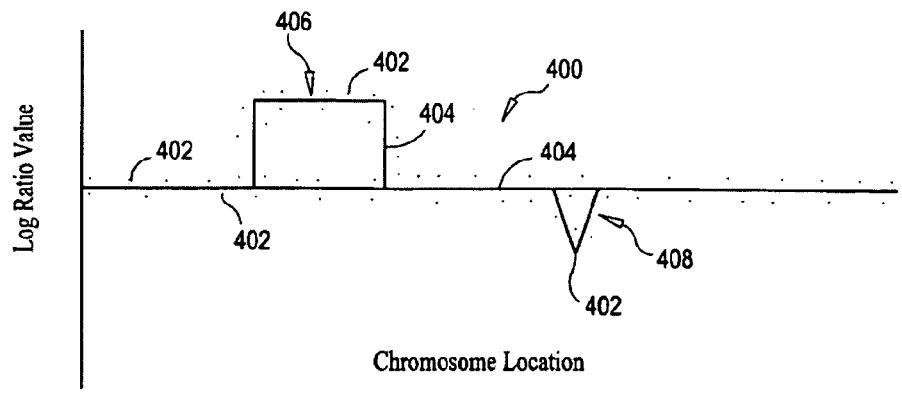
FIG. 4A, an illustration of a plot 400 of log ratio values between two channels from a CGH array.

When processing CGH arrays, it has been observed that the use of standard deviation of the negative control signals, or other noise estimate, may not estimate noise very well for CGH array applications, particularly in areas where duplication or amplification is reported. That is, it has been observed that noise levels for probes representative of chromosome locations where amplification or deletion has occurred have been observed to be higher than noise levels of probes representative of chromosome locations that are normal (i.e., no amplification or deletion occurring). FIGS. 4C-4D illustrate examples of these differences in noise levels, and are explained in more detail below.

A more robust estimate of noise characterizing a CGH array may be outputted by calculating the spread of the log ratio differences between consecutive probes along all chromosomes represented by the CGH array, divided by the square root of 2 to counteract the effect of noise averaging. Referring to FIG. 4A, an illustration of a plot 400 of log ratio values between two channels from a CGH array is provided. The probe signals from the array have been rearranged to correlate to their positions represented on the chromosomes in the plot 400, thereby mapping them to the chromosome locations (chromosomal coordinates represented by each probe, respectively), with log ratio values of the two channels for each location/probe represented by data points 402. That is, the probes, as arranged, are capable of hybridizing, under stringent conditions, to consecutive positions along a chromosome. Note that consecutive does not necessarily mean directly adjacent to, as consecutive arrangement is defined along a consistent direction. An average log ratio value line 404 has been drawn based upon the plotted points 402. Where the genetic material is "normal" and no amplification or deletion has been reported, the average log ratio signal is about zero, as shown, and is expected, since the fold number should be the same in both channels. When one channel represents abnormal tissue, such as cancer tissue, for example, and the other channel is a control channel representing normal or non-cancerous tissue, then the regions in which amplification or deletion has occurred in the cancerous or otherwise abnormal tissue shows up by log ratio values that deviate from zero, e.g., a value around +1 for an amplification of two, such as the amplification region 406 shown in FIG. 4A or a significantly negative value indicating a deletion, such as illustrated in region 408 in FIG. 4A. The amount of the negative value plotted depends on the average ploidy of the sample and the copy number of the deletion or amplification. For example, if the average ploidy is two, a 1:2 deletion will show a log ratio of about −0.7 to about −1.0. As another example, where the average ploidy is two, a 3:2 amplification (i.e., where the copy number in the abnormal tissue sample is three and the copy number of the normal tissue sample is 2) will show a log ratio of about 0.4 to about 0.6.

Figure 4B:
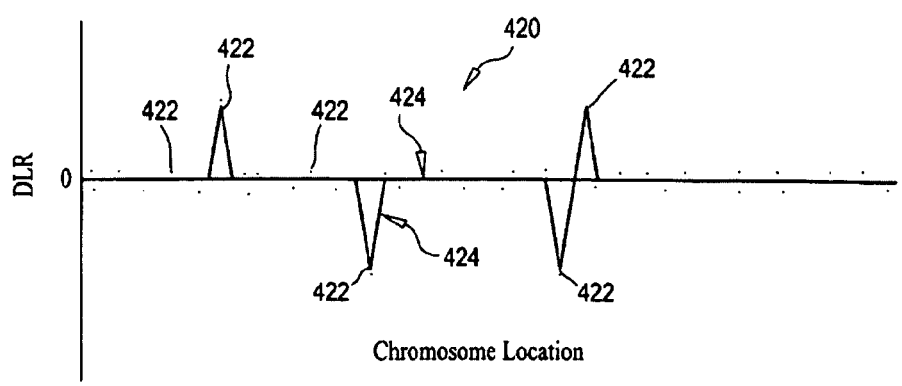
FIG. 4B illustrates a plot of the derivatives of the log ratio values plotted in FIG. 4A.
Figure 4C:
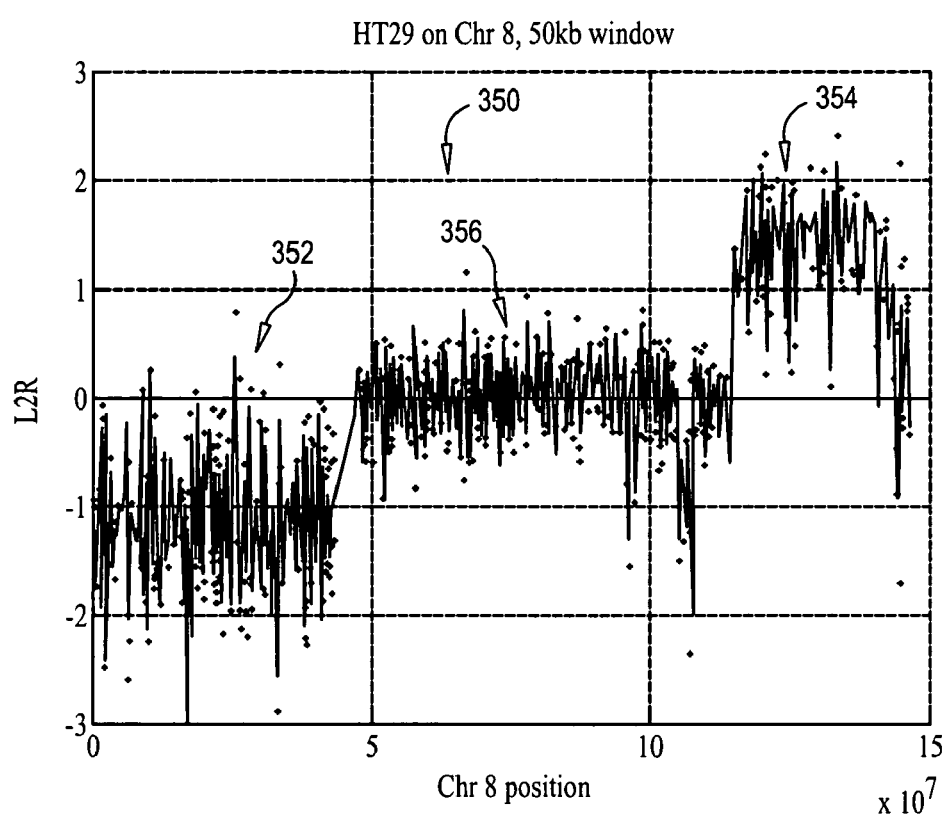
FIG. 4C illustrates the observed phenomenon that noise levels for probes representative of chromosome locations where amplification or deletion has occurred have been observed to be higher than noise levels of probes representative of chromosome locations that are normal (i.e., no amplification or deletion occurring).
Figure 4D:
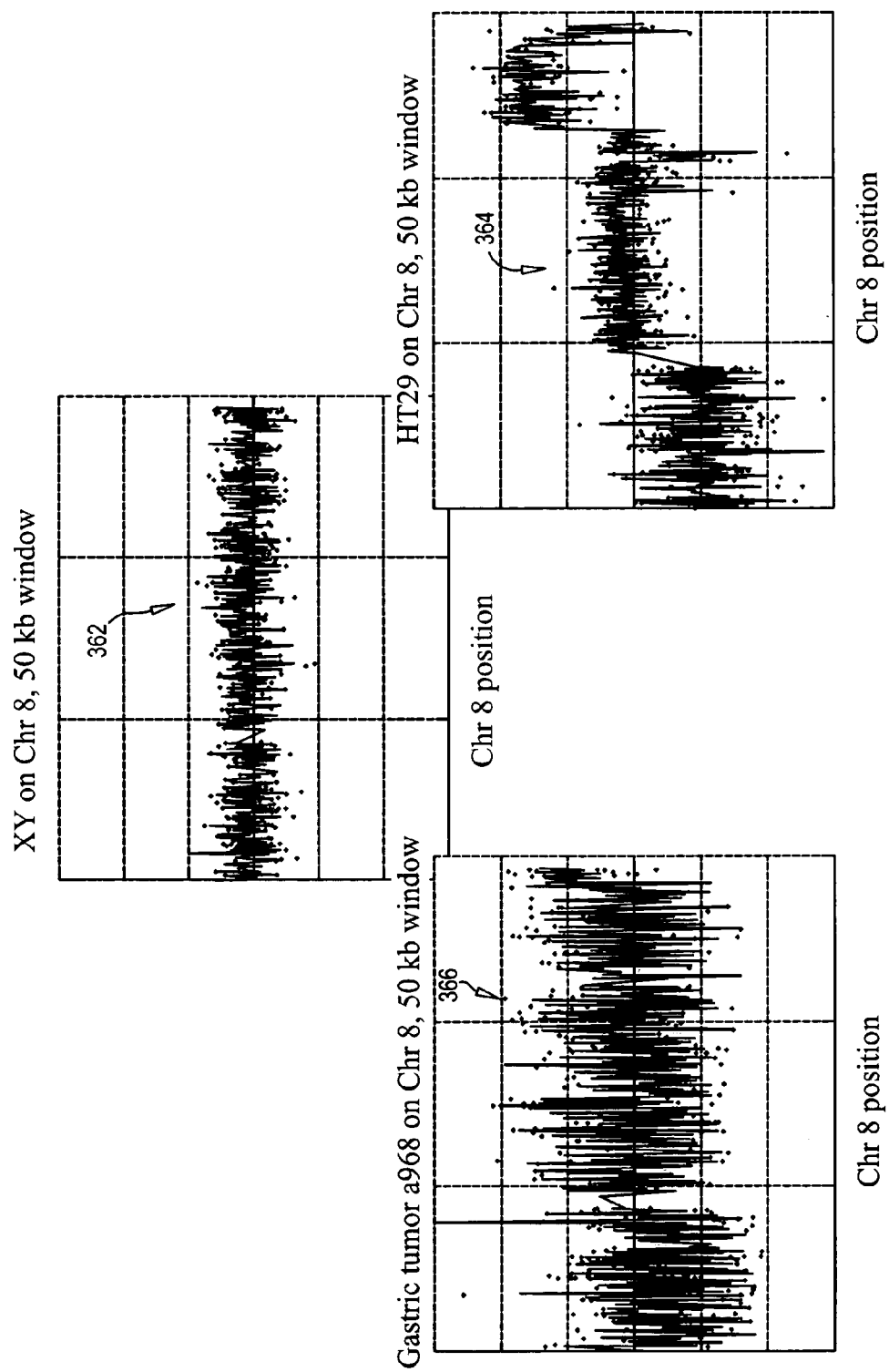
FIG. 4D is a display of charts comparing noise levels among diploid cell lines, aneuploid cell lines and tumor cell lines.

FIG. 4B illustrates a plot 420 of the derivatives of the log ratio values plotted in FIG. 4A. The derivative values are calculated by $DLR_i = LR_i - LR_{i-1}$, where DLRi is the derivative of the log ratio value at log ratio data point i, $LR_i$ is the log ratio value data point i and $LR_{i-1}$ is the i-$1^{st}$ log ratio data point, and i ranges from one to the total number of data points. The derivative values DLR are all around zero value on average, as indicated by average value line 424 plotted based upon DLR values 422, except for values that initially jump or drop to begin or end the indication of an amplification or deletion. An inter-quartile range of the DLR value 422 may be determined (e.g., by ranking the DLR values 422 from lowest to highest or highest to lowest, and then considering only those data points from the twenty-fifth percentile to the seventy-fifth percentile of the ranked range), to eliminate the outlier values, including those defining the spikes in the plot of FIG. 4B.

The DLR values in the inter-quartile range, referred to as DIQR are then mathematically converted according to the following formula to provide the spread of the derivative of log ratio values: Spread=(dIQR/erfinv(0.5)*2*√2/√2). The extra √2 division is needed to convert from derivative log ratio space to log ratio space, and erfinv(0.5)*2*√2 is a constant that compensates for use of the inter-quartile range as opposed to the entire range, based upon a normal distribution, where "erfinv" represents and inverse error function. Thus the spread of the derivative of log ratio values is determined as a measure of noise characterizing the array.

FIG. 4C illustrates the phenomenon described above, wherein it has been observed that noise levels for probes representative of chromosome locations where amplification or deletion has occurred have been observed to be higher than noise levels of probes representative of chromosome locations that are normal (i.e., no amplification or deletion occurring). A plot of the $\log_2$ standard deviation of noise for chromosome 8 in the ht29 cancer cell line is shown 350 in a 50 Kb window. The portion displayed has distinct regions of copy number loss 352 and copy number gain 354 relative to the region 356 showing normal copy number. It can be readily visually observed that the regions 352, 354 with copy numbers differing from the average ploidy of the genome are noisier than region 356 having the average ploidy, as deviation from a median value in those regions is greater than in region 356. Thus, the noise may be different in different locations of a sample measured, as noted, due to variations in ploidy. Using derivative log ratio noise calculation techniques described herein, the system identifies the ploidy of different parts of the genome and calculates the noise for those sections separately, rather than using one noise estimate for the entire array.

FIG. 4D is a display of charts comparing noise levels among diploid cell lines having been plotted 362 with noise levels associated with aneuploid cell lines having been plotted 364 and tumor cell lines 366. The $\log_2$ standard deviation of noise plotted with regard to the diploid cell lines 362 is less than about 0.2, while $\log_2$ standard deviation of noise plotted with regard to the aneuploid cell lines (HT29) is about 0.3 and $\log_2$ standard deviation of noise plotted with regard to the tumor cell lines 366 is greater still.

Figure 5:
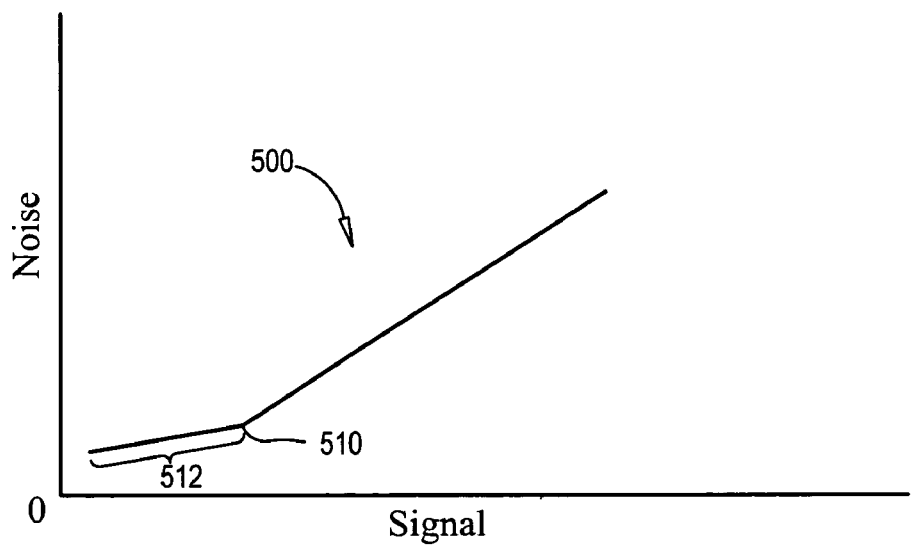
FIG. 5 illustrates the lack of proportionality of noise to signal at the low end of the signal range, and the proportionality of noise to signal at signal levels above some low level of signal.

A measure of intra-array reproducibility may be computed and outputted. This metric is based on analysis of replicated probes in the signal space. For each set of non-control replicated probes (i.e., control type=0, experimental probes, wherein a set of replicated probes is a set wherein each probe in the set is designed to bind with the same target), the % CV in the signal space is calculated. A plot of signal versus noise for the probes of an array will typically review that the noise level is generally proportional to the signal level above a minimum threshold signal level 510, as illustrated in plot 500. In range 512, the noise is considered to be additive, and not proportional to the signal. The probes that are reported in range 512 are not considered for the intra-array reproducibility metric, since the noise is not proportional to those signals. Noise in this case may be defined as an additive factor plus a multiplier (M) times the signal level. Therefore, in the very low signal range, such as range 512, the noise is dominated by the additive factor and that is why noise is not proportional to the signal level in that range. As the signal level increases, in the zone to the right of zone 512 in FIG. 5, the factor M times signal level becomes significantly greater then the additive factor and thus controls in the definition of noise. Therefore, noise becomes proportional to the signal level in this range. The multiplier M is dependent upon the array characteristics and may be measured offline, so that it is a known constant prior to this processing.

The intra-array reproducibility metric is calculated based on probes the signals of which are in the range where noise is substantially proportional to the signal level. Thus, probes for which the additive factor is less than M times the signal level are desired for performing the calculations. A proportional threshold may be calculated by multiplying the standard deviation of the background subtracted negative control signals (described above) by a proportionality multiplier, m. The proportionality multiplier m may be defined by m=1/M, M having been previously defined above. However, the proportionality multiplier m may be modifiable by a user. Non-control probes having replicates and a median signal greater than m*additive noise are then eligible for use in calculating the intra-array reproducibility metric.

The system may include an option for a user to set a minimum number of replicated probes that must be present on an array (and pass any filters applied) in order to be considered for calculation of the intra-array reproducibility metric. Alternatively, the system may include any non-control probes containing replicates that have passed any filters that have been applied.

For each set of probe replicates that has at least the minimum number of replicated probes (after removing any probes that do not pass the applied filter(s)), an average signal (e.g., mean signal) of each replicate probe set is calculated, wherein all signals considered are background subtracted signals. The standard deviation of the signals from each set of probe replicates described above is also calculated. Any replicated probe sets having a mean signal below the proportional threshold identified above are discarded from further use in the calculations. The remaining replicated probe sets are further processed to calculate a variation value among each remaining probe set. For example, a coefficient of variation (CV) for each remaining probe set may be calculated, where percentage CV=standard deviation of the probe set/mean of the probe set*100. The intra-array reproducibility metric is then calculated by calculating the median CV value of the groups of replicated probes considered.

Figure 6:
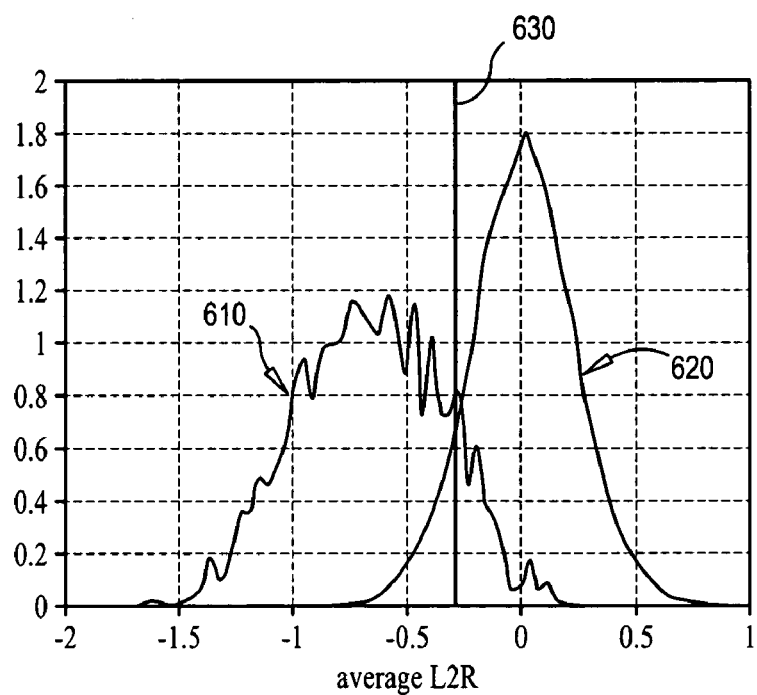
FIG. 6 shows log-ratio values (male/female) of X-chromosome probes and autosomes have been plotted with respect to number of probes (p).

Another metric analyzes a Receiver Operating Characteristic (ROC) curve to analyze false positive and true positive signals from a CGH array containing probes for normal male and female specimens, as read by a system (such as a scanner or other reader) on first and second channels, respectively (or, alternatively, a CGH array having probes for a normal male specimen and another CGH array having probes for a normal female specimen as read by a reader on a single channel, consecutively. Referring to FIG. 6, the log-ratio values (male/female) of X-chromosome probes and autosomes have been plotted with respect to number of probes (p), as plots 610 and 620, respectively. Filtering may be performed to remove outliers and or non-uniform features prior to plotting, so that only signals that pass the filtering process are plotted. The X-chromosome probes hybridize under stringent conditions to one or more sequences on the X-chromosome and the autosome probes are probe that hybridize under stringent conditions to one or more sequences on one or more different autosomes. The log ratio values are determined by comparing male to female samples for corresponding probes. Theoretically, the median average log-ratio value for the X-probes should be −1, and the median average log-ratio for the autosomes probes should be zero, with no overlap of the two curves. This metric provides a quantitative measure of how well, or close to ideal, that the system can detect the curves 610 and 620 in FIG. 6 and distinguish one from the other. Since the distributions, in real cases, will generally overlap, this metric endeavors to find the best cut-point (log ratio value) 630 above which the value will be considered a false positive value (i.e., not an X probe) and below which will be considered a true positive value (i.e., an X probe). An ROC curve may be calculated to determine the cut-point value.

Figure 7:
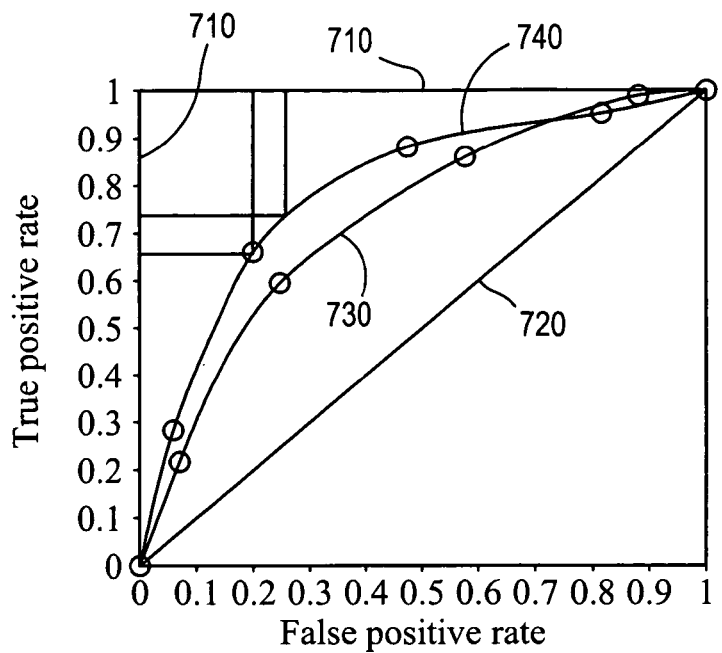
FIG. 7 illustrates various ROC curves.

An ROC curve is a graphical representation of the trade off between the false positive and true positive rates for every possible cut-point. By tradition, the ROC plot shows the false positive rate on the X-axis and the true positive rate on the Y-axis, as illustrated in FIG. 7. In the ideal, theoretical situation as described above, where the two curves are well separated, the resulting curve will closely follow curve 710. In the other extreme case, if the two distributions overlap completely, that the resulting ROC curve follows the diagonal (forty-five degree) line 720, as no distinction between true and false positives can be made. For all other intermediate case (e.g., real cases), the curves lie somewhere in-between, and curves 730 and 740 are exemplary of this.

To generate the ROC curve, the system sorts the log ratio signals over the entire array(s) in ascending order. Referring back to the description of FIG. 6, each log ratio value in the data set comes from an X probe or an autosome probe. All Y-chromosome probes are excluded for this purpose. Each log ratio value from an X probe contributes to the number of true positive (TP) data points and each log ratio value from an autosome probe contributes to the number of false positive (FP) data points. Starting from the lowest log ratio value in the sorted data set, TP is incremented by one for each X-probe log ratio value and FP is incremented by one for each autosome probe log ratio as the system reads through the sorted data set of log ratio values. For each log ratio value, the current FP value/total number of autosome probes is plotted versus the current TP value/total number of X probes. Hence the maximum value of both X and Y axes is 1. Another value called the error fraction is computed for each log ratio value, where error fraction=(FP/(total number of autosome probes)+(1− TP/total number of X probes))/2. The system then calculates the minimum value of all calculated error fraction values and reports this value. The range within which the minimum value will lie is between zero and one, with zero being the ideal theoretical case and one being the case where there is total overlap. Therefore, the closer that the calculated minimum value is to zero, the better the reported result. Another value that may be reported by the system is the difference between the median value of the X-probes plot and the median value of the autosome probes plot. In the example of FIG. 6, the difference between the median of the X-probes plot and the median of the autosome probes plot is −0.67. A third metric that may be calculated in this case is the area under the ROC curve, as this gives an objective, relative measure of the degree to which the curves (which form the basis for the data from which the ROC curve was generated) are separated.

Figure 8:
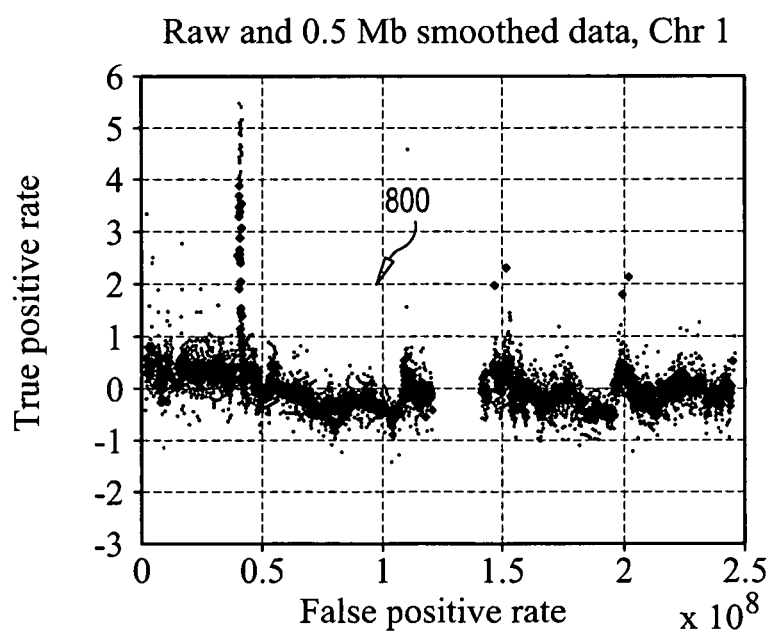
FIG. 8 shows an example of a wandering baseline with regard to $\log_2$ ratios and smoothed ratios plotted from chromosome 1 of a sample having poor representation.

One source of error in CGH assays comes from inconsistent amplification and/or labeling of different parts of the genome. This error manifests itself as a "wandering baseline", which may compromise the ability to clearly distinguish copy number changes in the result. This error is frequently seen after phi29 amplification of compromised samples. Assays afflicted by uneven genomic representation can score well on all of the other metrics described herein. As noted, poor representation may prevent clear-cut copy number calls and, therefore, unambiguous aberration detection. An example of a wandering baseline 800 is shown in FIG. 8 with regard to $\log_2$ ratios and smoothed ratios plotted from chromosome 1 of a sample having poor representation. The gap in the plotted date is representative of the centromere and is typical.

Figure 9B:
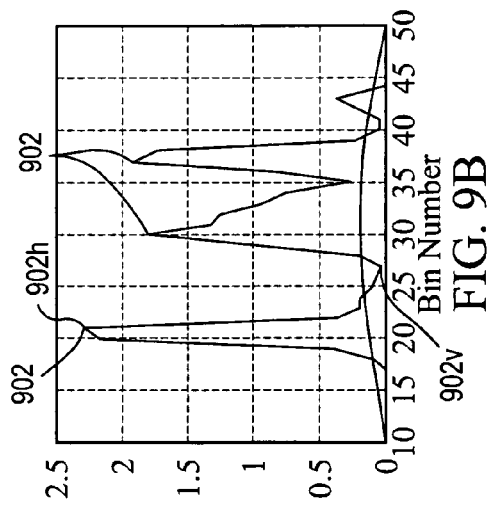
FIG. 9B shows a probability distribution plot of the smoothed, segmented log ratio data of FIG. 9A.
Figure 9A:
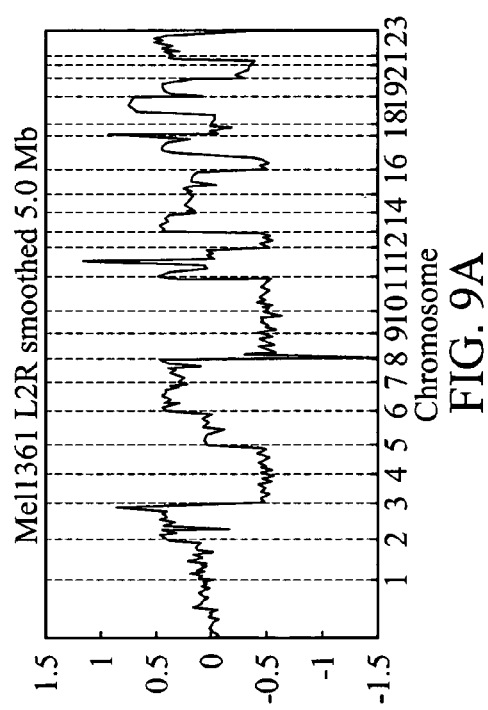
FIG. 9A shows a plot of log ratio data derived from two channels of CGH array data that has been heavily smoothed across the entire genome.

The systems may calculate a metric that directly measures copy number ambiguity according to the following. Initially, the genome is segmented by copy number, that is, separated into groups of log ratio values representing different copy number values. There are various schemes for segmenting the genome. One method is illustrated in FIGS. 9A-9B. The log ratio data derived from two channels of CGH array data are heavily smoothed across the entire genome, e.g., the example shown in FIG. 9A has been smoothed to 5.0 Mb, wherein the log ratio at each probe site is replaced by an average of the log ratios of all probes within 2.5 Mb on either side of that probe and including that probe. There are various algorithms available for accomplishing smoothing of this sort. Also, the smoothing does not have to be carried out over 5.0 Mb, but can be any other fairly large range, smaller or larger than 5.0 Mb. The probability distribution (e.g., a normalized histogram) of the smoothed, segmented log ratio data of FIG. 9A is then plotted at FIG. 9B. If the representation of the data is good, as in the case shown in FIG. 9B, then the plotted probability distribution of log ratios will show clear peaks 902 corresponding to integral copy numbers of the genetic material located at those coordinates. If the representation is poor, as in the case of the example in FIG. 8 and in FIGS. 10A-10B, there will be little or no separation between peaks 1002 and hence no unambiguous assignment of copy number can be made.

Figure 10B:
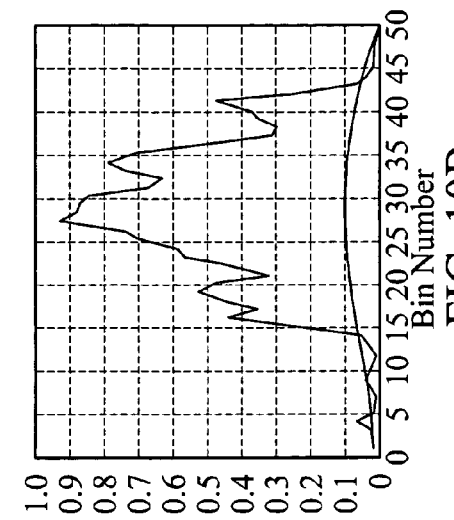
FIG. 10B shows a probability distribution plot of the smoothed, segmented log ratio data of FIG. 10A.
Figure 10A:
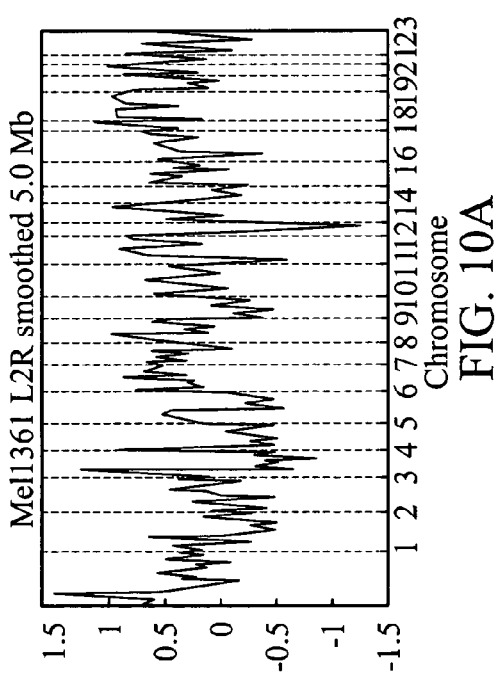
FIG. 10A shows another plot of log ratio data derived from two channels of CGH array data that has been heavily smoothed across the entire genome.

Once the peaks have been established, according to the above, the system then quantifies the separation between copy number peaks. Various metrics may be used to quantify the separation of the copy number peaks in the distributions. One example is by quantifying the difference in the height of the probability distribution between the highest peak 902$h$ and the lowest valley 902$v$ between peaks. This provides a general measure of the probability that an arbitrary probe will report an unambiguous copy number. For the example of FIG. 9B, the difference in height metric was calculated to be 2.16, while for the example of FIG. 10B, the difference in height metric was calculated to be 0.21. Note that the plotted curves in FIGS. 9B and 10B are of probability density. To determine the actual probability that a log ratio falls into a given range, an integration under the curve is performed for the log ratio. The total area under the curve is equal to 1.0, so the height of the curve isn't the probability, it is the derivative of the probability, which can be arbitrarily large.

In addition to automatically determining the peaks and quantifying the separation between copy number peaks, the system may also automatically calculate the nose separately for the different sections of the genome representing different copy numbers. For example, after heavily smoothing the log ratio data, such as in the manner described above, and plotting a distribution of the smoothed log ratio data, such as described with regard to FIG. 9B above, the width of each peak is determined in the distribution of smoothed log ratios. Next, for each peak, all probes within a predetermined log ratio distance (e.g., twice the peak width, although other predetermined distances may be substituted) of the peak are selected and each selected probe is marked or labeled with the value of the nearest copy number peak. These probes are then used to compute a local noise level for that peak or copy number.

The system next searches along the genome, identifying stretches that include only probes which are either unmarked (outliers), or marked with the same label. Such stretches are interpreted to be regions having the same copy number (regions of constant copy number). The local noise in each chromosomal region is then estimated as the standard deviation of the unsmoothed log ratio values of all marked probes contained in the nearest region of constant copy number.

There are several methods for automatically determining the ploidy of the plotted peaks from the smoothed log ratio data. The simplest is to arbitrarily assign the largest (most abundant) peak as diploid, and label the other peaks in counting sequence up and down from the diploid peak. A more reliable method determines the average ploidy of the sample using another technique, such as spectral karyotyping (SKY), for example, and assigns the most abundant peak to the average copy number as determined by the other technique. More complex heuristic methods, such as using the log ratio separation between peaks may alternatively be applied. Currently the system labels as diploid the most abundant of the tow peaks of lowest log ratio in the case where there is a diploid reference sample. That is, the peak at the lowest log ratio is called diploid if it is larger (more abundant) than the next lower peak or haploid if it is smaller (less abundant) than the next lower peak.

In addition to calculating and outputting the metrics described above, the system may also perform a run chart for multiple arrays. For example, all arrays in a multi-array experiment may be reported on by outputting metrics for each array in a single run chart. For example, one or more metrics may be plotted and/or outputted for each array considered. The system may provide outputs for each array per each metric calculated, or the system may optionally provide for user selection of which metrics to provide run chart outputs for. In either case, the values for a particular metric should be similar for all the arrays considered.

After calculating metrics for multiple arrays (for example, when multiple arrays are processed for an experiment), the calculated metrics may be displayed in a table 1100, as shown in FIG. 11. Each row of table 100 displays the various metrics having been calculated for the particular array 1102 that is displayed in that row, respectively. The "Design No." column includes a number for each respective array that identifies the particular design file containing parameters according to which the array was produced, for example, grid template, column spacings, subgrid row and column numbers, if applicable, spacings between subgrids, number of arrays/hybridizations on a slide, etc. The table 1100 may be scrollable using scroll bar 1122, for example to display metrics not currently shown on the display, when the number of metrics is too large to display all in one view.

The view in FIG. 11 shows a table of metrics for eleven arrays that have been feature extracted and processed to produce metrics according to techniques described herein. Column 1108 contains values for the DLR metric (spread of the log ratio differences) for each array. Columns 1110 and 1112 contain values for the signal to noise metric for first and second channels (r=red and g=green) for each array, as this is a dual channel study. Similarly, columns 1114 and 1116 contain values for the signal estimate metric for the first and second channels (r=red and g=green) for each array, and columns 1118 and 1120 contain values for the intra-array reproducibility metric for first and second channels (r=red and g=green) for each array. Although column 1120 is only partially shown in FIG. 11, it may be fully shown by scrolling to the right using scroll bar 1122.

In this table, a user may manually assign "pass", "fail" or "marginal" ratings to the arrays (and optionally, an N/A rating meaning that the array has not been rated), individually, based upon reviewing the reported metrics. Thus, by selecting a cell in the QC Status column 1106, the user is provided with a drop down menu or other selectable interface from which a rating of pass, fail or marginal (and optionally, N/A) may be selected. That is, if any one of the reported metrics exceeds a threshold value for that metric, the user may assign the array an overall fail rating. Also, if an array does not exceed the fail threshold, but exceeds another threshold value determined for marginality, or approaches the fail threshold closely, then the user may assign the array a marginal rating. By default, the system may initially assign a "pass" rating (or optionally, N/A) to each array.

Figure 12:
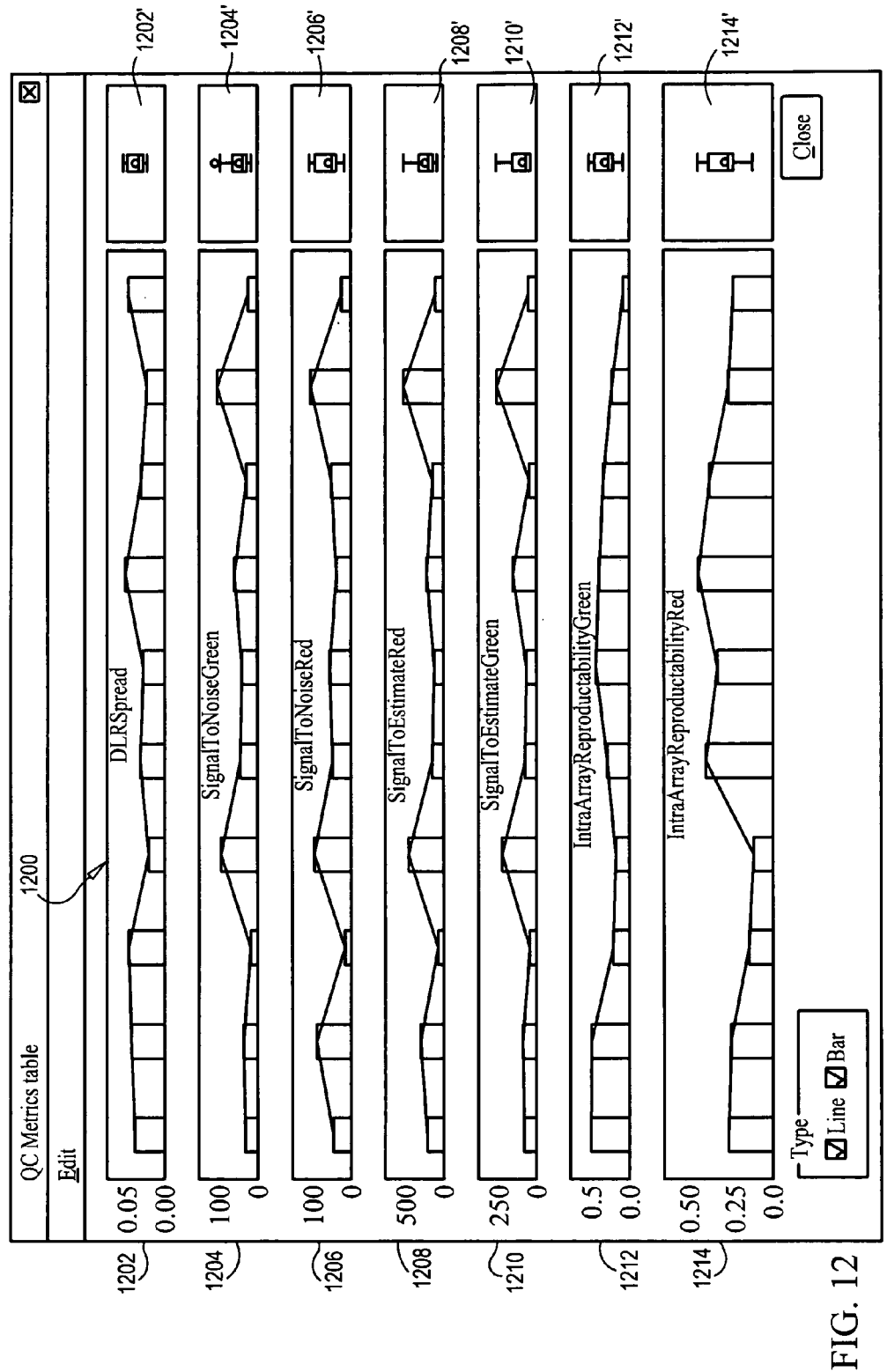
FIG. 12 shows a display of run charts created for the metrics shown in FIG. 11.

Run charts may also be produced by the system as noted above. FIG. 12 shows run charts created from the data from the ten CGH arrays that had metrics displayed therefore in the table 1100. For each run chart 1202, 1204, 1206, 1208, 1210, 1212, 1214 a bar is created for each array 1102, with the arrays displayed along the X-axis of the run chart and the height of each bar corresponding to the value of the particular metric being displayed in the run chart as it was reported for that particular array in table 1100, with values running along the Y-axis of each chart. Each run chart facilitates the visualization of variations in the values of the metrics calculated across the arrays that were processed. The system may also calculate the median and other values across the run chart, such as the $25^{th}$ and $75^{th}$ percentile values, for example, and graphically illustrate these at 1202', 1204', 1206', 1208', 1210', 1212', and 1214'. The median, $25^{th}$ and $75^{th}$ percentile values may be used to set thresholds for failed arrays and marginal arrays. These thresholds may be relied upon by the user in rating the arrays in the table 1100 in the manner described. Alternatively, the system may calculate thresholds based upon at least one of the median, $25^{th}$ and $75^{th}$ percentile values and automatically rate each array as pass, fail or marginal based upon the calculated thresholds.

Figure 13:
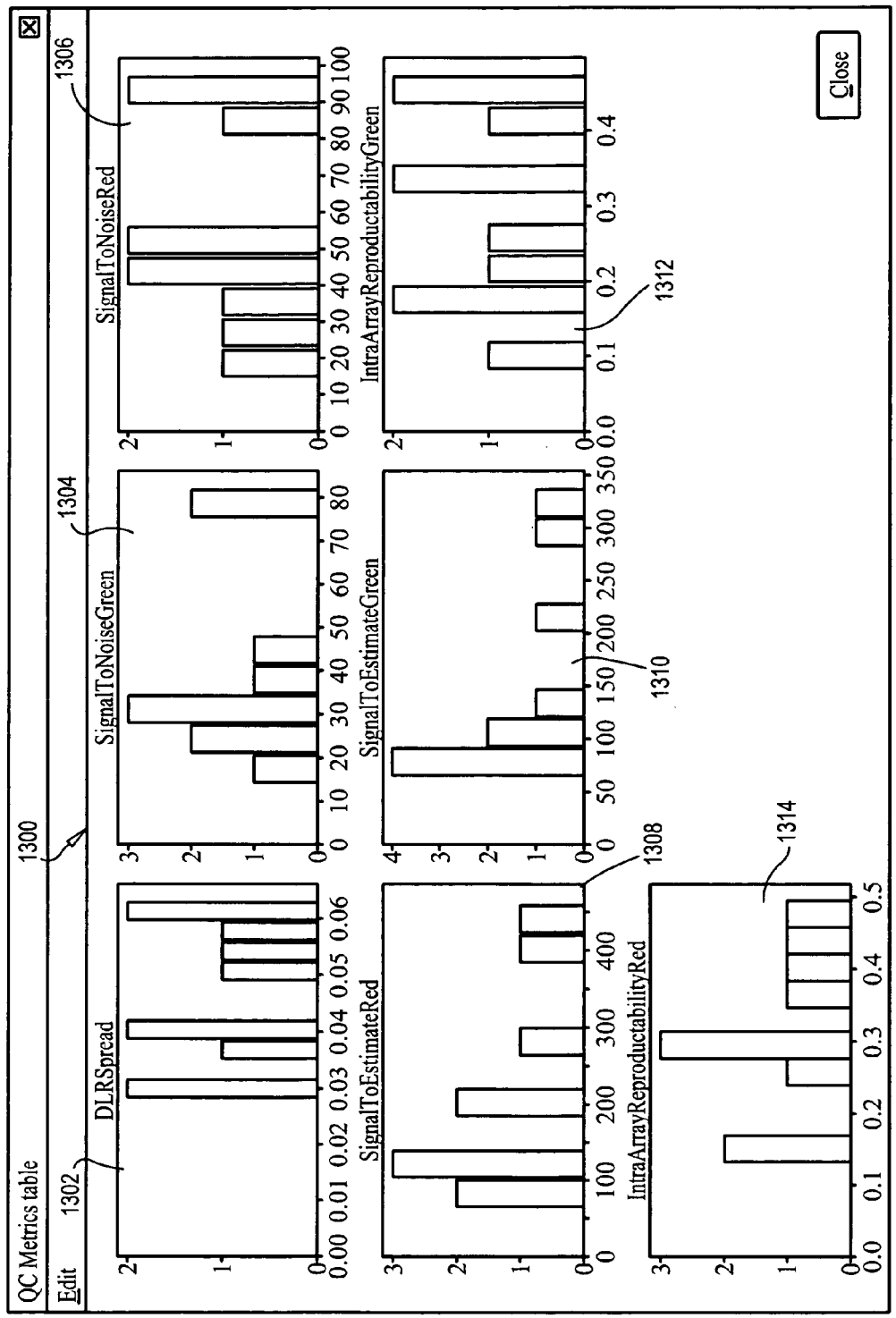
FIG. 13 shows histograms created from the metrics shown in FIG. 11.

The systems may also generate one or more histograms to illustrate the frequency distribution of metric values across the arrays being considered. FIG. 13 is an example of a display 1300 of histograms 1302, 1304, 1306, 1308, 1310, 1312, 1314 that the system generated for each of the metrics produced for each of the arrays in FIG. 11. In the histograms, each bar represent one bin produced by separating the entire set of metrics values into a plurality of bins, each bin representing a different value or ranging over a different value range for the metric. The height of each bar corresponds to the total number of metric values that are members of that bin, and this number is represented on the Y-axis. The metric values or value ranges are represented on the X-axis. From the distributions plotted in the histograms 13300, threshold values may also be calculated either manually or automatically for use in rating the individual arrays.

Figure 14:
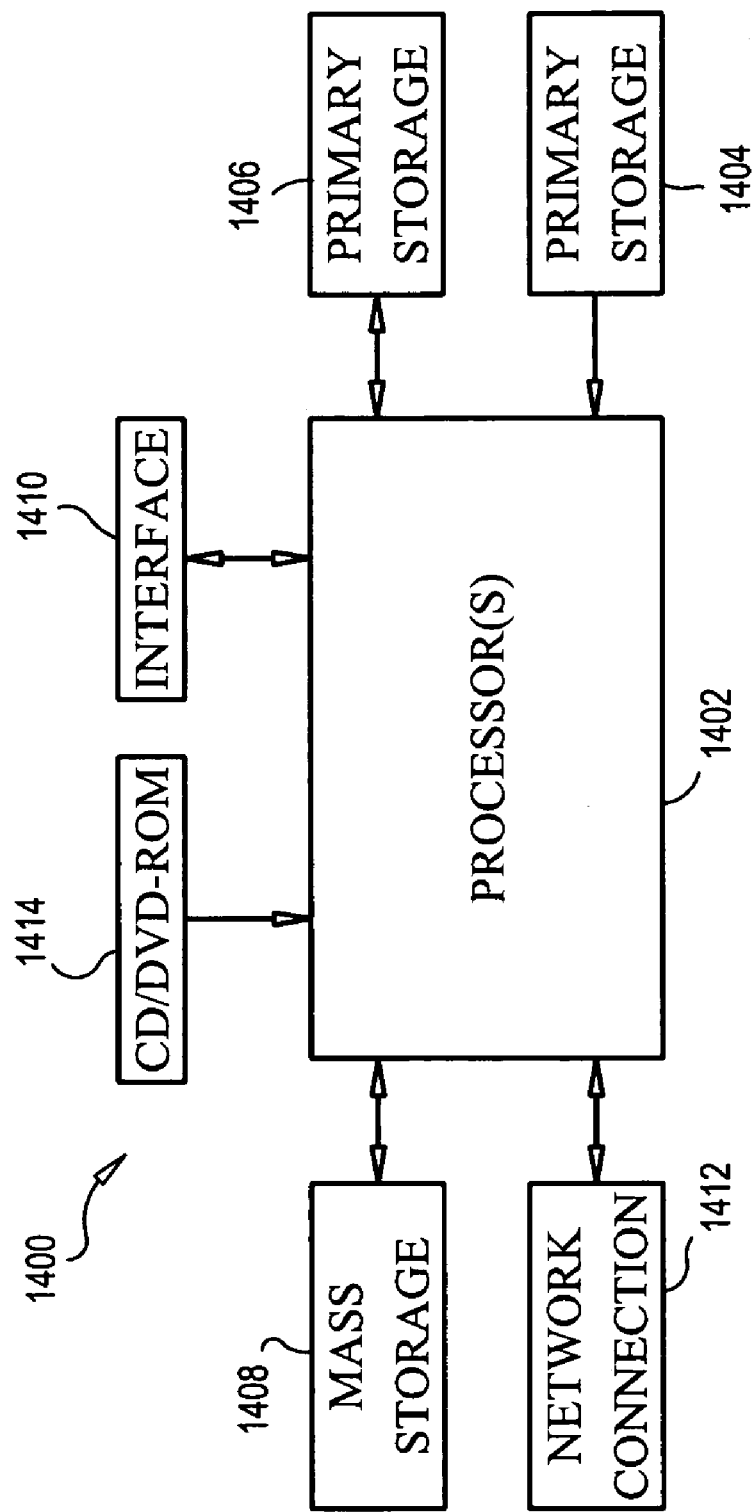
FIG. 14 is a schematic illustration of a typical computer system that may be used in performing procedures described herein.

FIG. 14 is a schematic illustration of a typical computer system that may be used to perform procedures described above. The computer system 1400 includes any number of processors 1402 (also referred to as central processing units, or CPUs) that are coupled to storage devices including primary storage 1406 (typically a random access memory, or RAM), primary storage 1404 (typically a read only memory, or ROM). As is well known in the art, primary storage 1404 acts to transfer data and instructions uni-directionally to the CPU and primary storage 1406 is used typically to transfer data and instructions in a bi-directional manner Both of these primary storage devices may include any suitable computer-readable media such as those described above. A mass storage device 1408 is also coupled bi-directionally to CPU 1402 and provides additional data storage capacity and may include any of the computer-readable media described above. Mass storage device 1408 may be used to store programs, data and the like and is typically a secondary storage medium such as a hard disk that is slower than primary storage. It will be appreciated that the information retained within the mass storage device 1408, may, in appropriate cases, be incorporated in standard fashion as part of primary storage 1406 as virtual memory. A specific mass storage device such as a CD-ROM or DVD-ROM 1414 may also pass data uni-directionally to the CPU.

CPU 1402 is also coupled to an interface 1410 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 1402 optionally may be coupled to a computer or telecommunications network using a network connection as shown generally at 1412. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for calculating statistical significance may be stored on mass storage device 1408 or 1414 and executed on CPU 1408 in conjunction with primary memory 1406.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A computer-implemented method of characterizing quality of hybridized CGH arrays, said method comprising:
    computer generating at least one metric for a CGH array that characterizes a property of the CGH array, wherein said generating at least one metric comprises calculating a spread of the differences in log ratio values between consecutive probes representing consecutive positions along a chromosome, wherein said log ratio values are calculated by a signal value from one channel of the CGH array relative to a second channel of the CGH array or a channel of another CGH array;
    repeating said computer generating at least one metric for at least one additional CGH array;
    comparing each metric across all CGH array metric values generated to identify a quality of any one of the CGH arrays characterized, relative to the CGH arrays characterized for that metric; and
    outputting the metrics for use by a human user.

2. The method of claim 1, wherein said outputting comprises displaying the metrics in a QC report on a display.

3. The method of claim 2, wherein said spread of the differences in log ratio values metric is displayed with regard to all the CGH arrays from which that metric was generated, respectively.

4. The method of claim 1, wherein a plurality of different metrics are generated for each CGH array, and wherein said metrics are reported in the QC report with a separate report for each metric generated, relative to values for the CGH arrays from which that metric was generated.

5. The method of claim 1, wherein the spread of the differences in log ratio values is divided by the square root of two.

6. A computer-implemented method of determining the quality of a CGH array, said method comprising calculating, via a computer, a spread of the differences in log ratio values between consecutive probes representing consecutive positions along a chromosome, wherein said log ratio values are calculated, via the computer, from probe signals from a CGH array, as read by a reader on first and second channels thereof, or from probes signals from two CGH arrays, as read by a single channel reader; and outputting the calculated spread for use by a human user.

7. The method of claim 6, wherein the spread of the differences in log ratio values is divided by the square root of two.

8. The method of claim 2, wherein said displaying includes displaying the metrics in a metrics table.

* * * * *